United States Patent
Lazzara et al.

[11] Patent Number: 5,899,697
[45] Date of Patent: May 4, 1999

[54] ANATOMIC INTERCHANGEABLE HEALING ABUTMENT AND IMPRESSION COPING

[75] Inventors: Richard J. Lazzara, Lake Worth; Keith D. Beaty, Palm Beach Gardens, both of Fla.

[73] Assignee: Implant Innovations, Inc., Palm Beach Gardens, Fla.

[21] Appl. No.: 08/914,414

[22] Filed: Aug. 19, 1997

Related U.S. Application Data

[62] Division of application No. 08/337,387, Nov. 8, 1994.

[51] Int. Cl.⁶ ............................................. A61C 8/00
[52] U.S. Cl. ................................................. 433/173
[58] Field of Search ................................. 433/172, 173, 433/174, 175, 176

[56] References Cited

U.S. PATENT DOCUMENTS

| | | | |
|---|---|---|---|
| 4,758,161 | 7/1988 | Niznick | 433/173 |
| 4,850,870 | 7/1989 | Lazzara et al. | 433/174 |
| 4,850,873 | 7/1989 | Lazzara et al. | 433/220 |
| 4,856,994 | 8/1989 | Lazzara et al. | 433/173 |
| 4,955,811 | 9/1990 | Lazzara et al. | 433/173 |
| 4,988,298 | 1/1991 | Lazzara et al. | 433/173 |
| 5,006,069 | 4/1991 | Lazzara et al. | 433/173 |
| 5,015,186 | 5/1991 | Detsch | 433/173 |
| 5,030,096 | 7/1991 | Hurson et al. | 433/173 |
| 5,035,619 | 7/1991 | Daftary | 433/173 |
| 5,040,983 | 8/1991 | Binon | 433/173 |
| 5,071,351 | 12/1991 | Green, Jr. et al. | 433/173 |
| 5,073,111 | 12/1991 | Daftary | 433/173 |
| 5,100,323 | 3/1992 | Friedman et al. | 433/173 |
| 5,125,841 | 6/1992 | Carlsson et al. | 433/213 |
| 5,135,395 | 8/1992 | Marlin | 433/174 |
| 5,145,371 | 9/1992 | Jörnéus | 433/173 |
| 5,145,372 | 9/1992 | Daftary et al. | 433/173 |
| 5,154,612 | 10/1992 | Carlsson et al. | 433/173 |
| 5,188,800 | 2/1993 | Green, Jr. et al. | 422/23 |
| 5,209,659 | 5/1993 | Friedman et al. | 433/173 |
| 5,209,666 | 5/1993 | Balfour et al. | 433/173 |
| 5,213,502 | 5/1993 | Daftary | 433/172 |
| 5,246,370 | 9/1993 | Coatoam | 433/173 |
| 5,281,140 | 1/1994 | Niznick | 433/172 |
| 5,292,252 | 3/1994 | Nickerson et al. | 433/173 |
| 5,297,963 | 3/1994 | Daftary | 433/172 |
| 5,316,476 | 5/1994 | Krauser | 433/173 |

(List continued on next page.)

FOREIGN PATENT DOCUMENTS 0 657 146 A1  6/1995  European Pat. Off.  ..........  A61C 8/00

OTHER PUBLICATIONS

Exhibit A, drawing of a healing abutment.
Exhibit B, assembly drawing of a coping and the component drawings which comprise the coping assembly.
Exhibit C, one piece healing abutment made entirely of Deltrin™.
Perri, George, DDS et al., *Single Tooth Implants*, CDA Journal, vol. 17, No. 3, Mar. 1989.
DIA™ Dental Imaging Associates, Implamed –The Source, *The Anatomical Abutment System*, pp. 1–10, Oct. 9, 1991.
Lewis, S.G., et al., *Single Tooth Implant Supported Restorations*, Intnatl. Jrnl. of Oral & Maxillofacial Implants, vol. 3, No.1, pp. 25–30, 1988.
Lewis, S.G., et al., *The "UCLA"Abutment*, Intnatl. Jrnl. of Oral & Maxillofacial Implants, vol. 3, No. 3, pp. 183–189, 1988.

*Primary Examiner*—Nicholas D. Lucchesi
*Attorney, Agent, or Firm*—Arnold White & Durkee

[57] ABSTRACT

Dental restoration components for use to make a replacement tooth which substantially mimics the emergence profile of a natural tooth comprising two parts, one being a core adapted for fixation subgingivally in the site of the natural tooth, and the other being an emergence-profiler guide which fits on the core and shapes the overlying gingiva to the desired emergence profile. Two sets of the components may be provided, one for use as a healing abutment, and the other for use as an impression coping.

36 Claims, 2 Drawing Sheets

U.S. PATENT DOCUMENTS

| | | | |
|---|---|---|---|
| 5,334,024 | 8/1994 | Niznick | 433/173 |
| 5,336,090 | 8/1994 | Wilson, Jr. et al. | 433/172 |
| 5,338,196 | 8/1994 | Beaty et al. | 433/172 |
| 5,362,235 | 11/1994 | Daftary | 433/172 |
| 5,368,483 | 11/1994 | Sutter et al. | 433/173 |
| 5,419,702 | 5/1995 | Beaty et al. | 433/214 |
| 5,431,567 | 7/1995 | Daftary | 433/172 |
| 5,476,382 | 12/1995 | Daftary | 433/172 |
| 5,476,383 | 12/1995 | Beaty et al. | 433/214 |
| 5,492,471 | 2/1996 | Singer | 433/172 |
| 5,651,675 | 7/1997 | Singer | 433/172 |
| 5,662,476 | 9/1997 | Ingber et al. | 433/213 |
| 5,674,069 | 10/1997 | Osorio | 433/172 |
| 5,674,071 | 10/1997 | Beaty et al. | 433/172 |
| 5,674,073 | 10/1997 | Ingber et al. | 433/213 |

ANATOMIC INTERCHANGEABLE HEALING ABUTMENT AND IMPRESSION COPING

This application division of application Ser. No. 08/337,387 filed Nov. 08, 1994.

This invention relates to the art of preparing dental restorations that closely replicate natural dentition in appearance, contour and dimensions, especially where the teeth emerge from the gums. More particularly, this invention addresses the task of providing an improved emergence profile for an artificial tooth which will closely replicate the emergence profile of the natural tooth that it replaces no matter what the size and shape of the emergence profile of that tooth may have been. The invention of this application is related to the invention of application Ser. No. 08/043,928 filed Apr. 8, 1993 and allowed Feb. 14, 1994, both applications being commonly owned.

BACKGROUND OF THE INVENTION

For artificial teeth (commonly called "dental restorations") closely to replicate the lost natural teeth that they replace the artificial teeth must appear to emerge from the gums with the same shapes and contours that natural teeth have as they emerge from the gums. The increasing availability of dental implants, particularly osseointegrated implants, to serve as artificial roots, has provided opportunities to address this problem using techniques for fabricating implant-supported restorations directly to implants. Such a technique is described in published articles which appeared in The International Journal of Oral & Maxillofacial Implants, Vol. 3, Number 1, 1988 at pages 25–26 "Single-Tooth Implant Supported Restorations" Lewis, S. G. et al., and Number 3, 1988 at pages 183–189 "The "UCLA" Abutment", Lewis, S. et al. A similar result using a different abutment is described in U. S. Pat. No. 4,988,298, which is owned by the Assignee of the present invention. The problem is incompletely addressed in U. S. Pat. No. 5,073,522 issued to Daftary Dec. 17, 1991.

In general, the existing techniques are done using components which function to expand a transmucosal opening from the round size of the implant to a larger round size that more nearly approximates the size of the tooth where it emerges from the gum. The above-mentioned application Ser. No. 08/043,928 teaches a method and means to expand a transmucosal opening from the round size of the implant to a larger non-round size that more nearly approximates the size and the shape of the tooth where it emerges from the gum. The present invention further improves the art with a system of interchangeable components which enables low cost and convenient replication of the emergence profiles of all the different sizes and shapes of human teeth.

GENERAL NATURE OF THE INVENTION

Generally, the invention provides a pair of substantially identical core abutments, one to be used to support a healing abutment, and the other to be used to support an impression coping, together with a set of identical pairs of anatomic emergence-profiler healing abutment and impression coping formers, or guides, which are interchangeably mountable on the core abutments. Each set replicates the emergence profile of one type of natural tooth—e.g: molar, premolar, bicuspid, incisor, etc. The core abutments are made of a rigid material that can be made in precise dimensions, such as titanium. The emergence-profiler abutment and coping formers or guides are made of a low cost moldable material, such as a plastics material (e.g: acrylic) that is acceptable for dental use, and are preferably disposable, so that they can be used for one patient only and can if necessary be modified at chair-side. The emergence-profiler abutment guides replicate the emergence profile of the tooth that is to be restored, but they are made so short that they need not have occlusive surfaces, and the core abutments used to support them are similarly shortened. The emergence-profiler coping guides may be similarly short, in fact they may be identical to their corresponding emergence-profiler abutment guides, but the core abutments used to support the emergence-profiler coping guides may be longer for engagement in the materials used to take impressions, and may be fitted with means to retain them in the impression material. The invention has as its principal object to provide low-cost, reliable and precise method and means to realize the invention of the above-mentioned application Ser. No. 08/043,928. Like the invention of that application, the invention of the present application can be used to make stone models and soft tissue models of a patient's case.

DETAILED DESCRIPTION OF THE DRAWINGS

Figure 1:
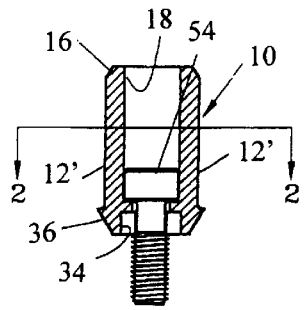
FIG. 1 is a longitudinal section through a core abutment according to the invention.
Figure 2:
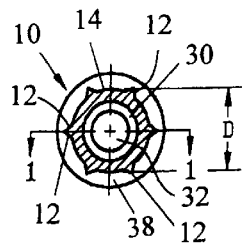
FIG. 2 is a transverse section through FIG. 1.
Figure 3:
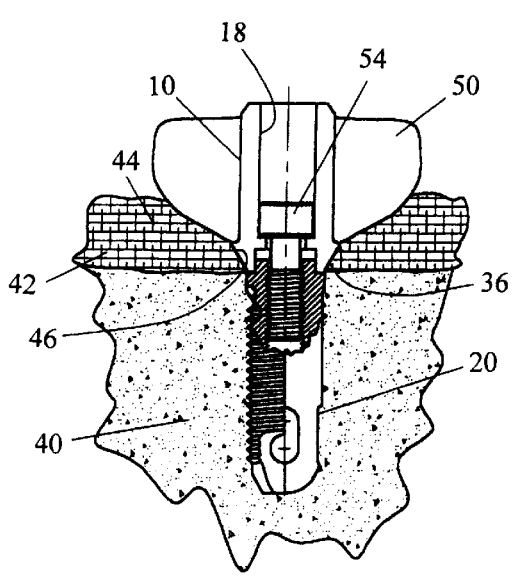
FIG. 3 is a side view of a healing abutment assembled on a dental implant.

Referring first to FIGS. 1 to 3, a core component 10 is generally tubular in form with an outer diameter "D" substantially the same as the diameter of the implant 20 (FIG. 3) on which it is to be mounted. Longitudinally-oriented ribs 12 are on the outer surface 14 which defines the diameter "D". Preferably, the ribs 12 have sharp edges 12', seen in FIG. 1. The ends 16 of the ribs at the supragingival end 18 of the core component are sloped toward the sharp edges. Six ribs are illustrated in FIG. 2, but the number of ribs can be different. In other structural respects that are illustrated in the drawings, the core components are similar to known abutments; that is, the transverse member 30 defining a screw hole 32 and the top surface of a hexagonal socket 34, and the expanded subgingival end 36 with its shoulder 38, are known features of existing abutments.

Figure 4:
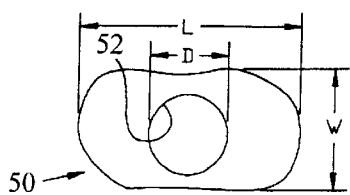
FIG. 4 is a top view of a emergence-profiler component of the invention.

In FIG. 3 the core component 10 is shown installed on a dental implant 20 which is fixed in bone 40 having overlying gingiva 42 with an aperture 46 giving access to the implant. As is the prevailing dental practice, the implant is substantially entirely encased in the bone, and the subgingival end 36 is mated to the implant, through the aperture, within the gingiva, at the junction of the gingiva and the bone. The emergence profile to be given to the aperture 46 through the gingiva will depend on the type of tooth that was in the site where the implant is now installed. FIGS. 3 and 4 illustrate a molar-type emergence-profiler abutment guide 50, for use as a healing component, having a mesial-distal dimension "L" and a buccal-labial dimension "W" which are characteristic of that type. A hole 52 through this abutment guide has the same diameter "D" as the core component 10. In use the healing component 50 is forced over the core component 10 so that the ribs 12 become embedded in the walls of the hole 52 until the healing component is seated on the shoulder 38. The assembly of both components is then attached to the implant in known fashion, using an abutment screw 54. The core component 10 is thereby fixed non-rotatively on the implant 20, and the healing component 50 is thereby fixed non-rotatively on the core component.

Figure 5:
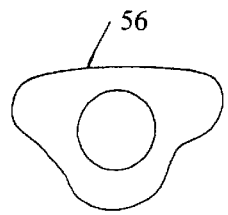
FIG. 5 is a top view of another emergence profiler component.

As is apparent in FIGS. 3 and 4, the healing component is now fixed in a position to force the aperture 46 to heal in a contour which closely replicates the emergence profile of a premolar-type tooth. FIG. 5 illustrates an alternative healing component 56 that can be used for restoration of another type tooth. It will be apparent that pairs of such tooth-shaped components can be provided at low cost in a wide variety of shapes, contours and sizes for a wide variety of tooth types.

Figure 6:
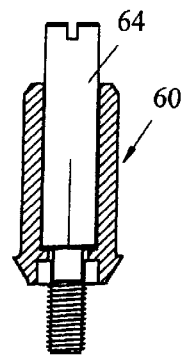
FIG. 6 is a longitudinal section through a core abutment for use as a pick-up type transfer coping.
Figure 7:
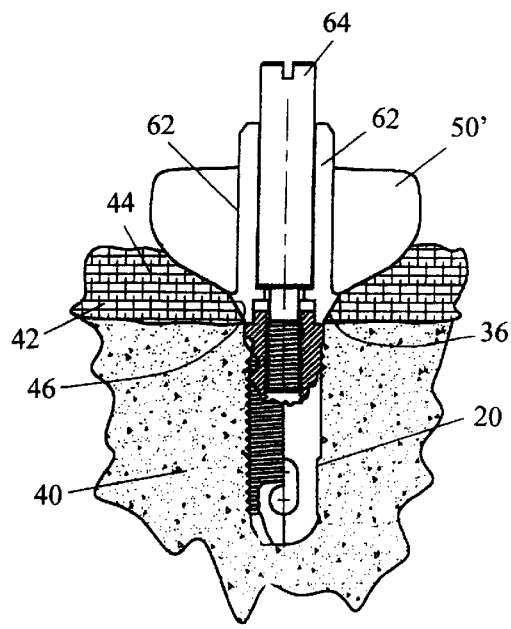
FIG. 7 is a side view of a pick-up type transfer coping assembled on a dental implant.

Referring now to FIGS. 6 and 7, the invention is there illustrated as it may be used to take an impression preparatory to making a laboratory model. A core abutment 60 intended for use as a pick-up type impression coping is longer than the core abutment 10, and a pick-up type coping screw 64 replaces the abutment screw 54. Otherwise the two core abutments are substantially identical. In use, the healing component 50 and its core component 10 are removed together, as a unit, from the implant 20, the longer core abutment 60 is non-rotatively attached to the implant with the coping screw, and a second premolar-type emergence-profiler guide 50', intended for use as an impression coping component, which may be identical to the first premolar-type component 50, is fitted over the core abutment 60 engaging the ribs 62 while oriented identically to the healing component 50. This assembly 50'-60 can then function as a pick-up impression coping in know fashion. The protruding supragingival end of the core component 60, together with the portion of the emergence-profiler guide 50' which extends above the gum 44, will serve to retain the coping in the impression material (not shown). The coping screw 64 will extend through the impression tray (not shown) where it can be accessed to separate the impression coping assembly 50'-60 from the implant, allowing the coping assembly to be "picked-up", or retained in the impression for use in making a model of the site.

Figures 8, 9:
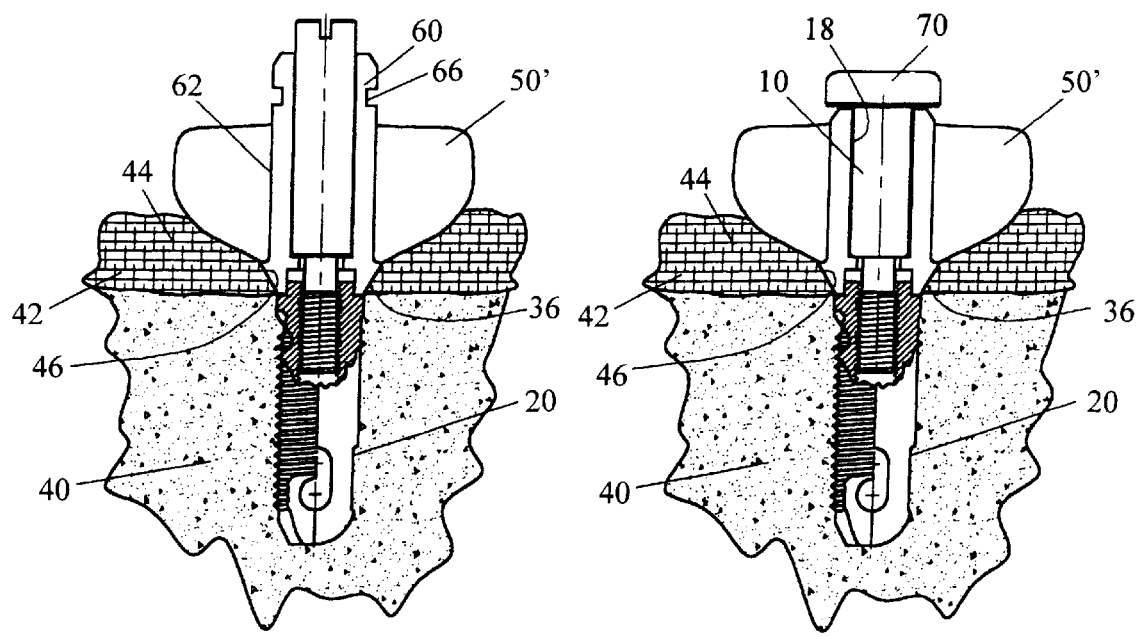
FIG. 8 is another embodiment of a pick-up transfer coping.
FIG. 9 shows another transfer coping according to the invention.
Figure 10:
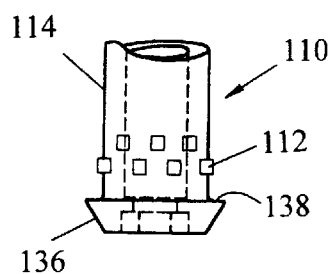
FIG. 10 is a side view of another core component.
Figure 11:
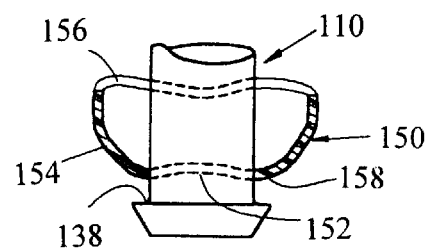
FIG. 11 is a section through another embodiment of the profiler guide.

Additional means to retain the pick-up coping assembly in impression material may be provided, in the form of an annular groove 66 on the core abutment 60, as is shown in FIG. 8, for example. In this embodiment, the groove 66 is preferably located closely above the top surface of the impression coping component 50', where impression material that flows into the groove can serve to lock the coping component 50' in place on the core abutment. Another alternative is to employ the shorter abutment 10 with a wide-headed impression-coping screw 70, like that shown in U.S. Pat. No. 4,955,811 owned by the assignee of this application, as is illustrated in FIG. 9. In this embodiment the transfer coping that results is not a pick-up coping. FIGS. 10 and 11 illustrate another embodiment of the invention employing a hollow-shell form 154 to make the emergence-profiler guide member 150 of the invention. The shell form can be, for example, blow-molded of a plastics material with an outer shape and contour to mimic a natural tooth. The shell has a round hole 152 in its bottom 158 through which a core component 110 can pass. Like the bore 52 in FIG. 4, this hole 152 has a diameter sized to fit closely around the core component. In use the shell 154 is fitted onto the core component 110 with its bottom 158 seated on the shoulder 138 on the subgingival end 136 and the shell is then filled, preferably to its rim 156, around the tubular part of the core component, with a flowable filling material such as an acrylic (not shown) intended for dental use, which hardens to form a substantially solid body within the shell, thereby providing a substantially solid emergence-profiler guide. The use of a flowable filling material allows the core component 110 to have multi-dimensional locking means such as projections 112 on its outer surface 114. Except for this unique difference the core component may be identical to the core components 10 or 60.

The invention thereby provides a new, accurate and inexpensive method and means for making and using an impression coping that faithfully reproduces the emergence profile established in the gingiva by the healing abutment component, and that can faithfully and accurately transfer that information to a working model in order to build an anatomically-shaped artificial tooth on a round-shaped implant.

The invention lends itself to the provision of temporary dentition. For example, the healing abutment can also function as a temporary tooth, albeit one lacking an occlusal surface. If an occlusal surface is desired the dentist can provide one by adding temporary tooth material (e.g: acrylic) to the top surface of the emergence-profiler guide 50.

We claim:

1. A set of dental components for making a replacement tooth generally mimicking a contour and dimensions of an emergence profile of a natural tooth through gingiva overlying root means, said gingiva having an aperture to said root means, said set comprising:

a first core for extending through said aperture in said gingiva;

means for fixing said first core subgingivally on said root means;

an emergence-profiler healing guide including a shell with a plastic outer surface which is contoured for forming said emergence profile in said aperture and a filling material to be placed within said shell around said first core;

means for attaching said emergence-profiler healing guide to said first core with said plastic surface of said shell located in said aperture;

a second core for extending through said aperture in said gingiva;

means for fixing said second core subgingivally on said root means;

an emergence-profiler coping guide including a shell with a plastic outer surface which is contoured for substantially fitting within said aperture and a filling material to be placed within said shell around said second core; and means for attaching said emergence-profiler coping guide to said second core with said plastic outer surface of said shell located in said aperture.

2. The set of dental components of claim 1 in which said emergence-profiler healing and coping guides are substantially identical.

3. The set of dental components of claim 1 in which said first and second cores have a cylindrical external shape and substantially a same outer diametric dimension, each of said cores being adapted at a first end thereof for fixation on said root means.

4. The set of dental components of claim 3 in which each of said emergence-profiler healing and coping guides has a hole therethrough, an internal shape of each of said holes being substantially the same as an outer shape of a corresponding one of said cores, each of said emergence-profiler healing and coping guides can be interchangeably fitted over each of said cores.

5. The set of dental components of claim 4 in which each of said cores has on an outer surface means for restraining said emergence-profiler healing and coping guides from rotating therearound.

6. The set of dental components of claim 1 in which said first core has a surface forming a section of said emergence profile in said aperture.

7. The set of dental components of claim 6 in which said second core has a surface for substantially fitting within said section of said emergence profile in said aperture formed by said surface of said first core.

8. The set of dental components of claim 1 in which said emergence-profiler coping guide is a transfer coping.

9. The set of dental components of claim 8 in which said means for attaching said emergence-profiler coping guide to said second core is a wide-headed impression-coping screw.

10. The set of dental components of claim 8 in which said first and second cores are substantially the same length.

11. The set of dental components of claim 1 in which said emergence-profiler coping guide is a pick-up coping.

12. The set of dental components of claim 11 in which said second core is longer than said first core.

13. The set of dental components of claim 12 in which said second core has means for retaining said second core in impression material, said retaining means including a groove.

14. A set of dental components for making a replacement tooth generally mimicking a contour and dimensions of an emergence profile of a natural tooth through gingiva overlying the root means, said gingiva having an aperture to said root means, said set comprising:

a first core for extending through said aperture in said gingiva, said first core for being attached on said root means;

an emergence-profiler healing guide including a shell with a plastic outer surface which is contoured for forming said emergence profile in said aperture and a filling material to be placed in said shell around said first core, said emergence-profiler healing guide for surrounding and engaging said first core;

a second core for extending through said aperture in said gingiva, said second core for being attached on said root means; and an emergence-profiler coping guide including a shell with a plastic outer surface which is contoured for substantially fitting within said emergence profile in said aperture and a filling material in said shell around said second core, said emergence-profiler coping guide for surrounding and engaging said first core.

15. The set of dental components of claim 14 wherein each of said first and second cores has a structure for locking said filling material thereon.

16. A set of dental components for making a replacement tooth generally mimicking a contour and dimensions of an emergence profile of a natural tooth through gingiva overlying root means, said gingiva having an aperture to said root means, said set comprising:

a first core for extending through said aperture in said gingiva;

means for fixing said first core subgingivally on said root means;

an emergence-profiler healing guide having an exterior surface contoured and dimensioned for forming said emergence profile in said aperture, said exterior surface being made of a plastic material;

means for attaching said emergence-profiler healing guide to said first core with said exterior surface located in said aperture;

a second core for extending through said aperture in said gingiva;

means for fixing said second core-subgingivally on said root means;

an emergence-profiler coping guide having an exterior surface contoured and dimensioned for substantially fitting within said aperture, said exterior surface being made of a plastic material; and means for attaching said emergence-profiler coping guide to said second core with said exterior surface located in said aperture.

17. The set of dental components of claim 16 in which said emergence-profiler healing and coping guides are substantially identical.

18. The set of dental components of claim 16 in which each of said emergence-profiler healing and coping guides has a hole therethrough, an internal shape of each of said holes being substantially the same as an outer shape of a corresponding one of said cores.

19. The set of dental components of claim 18 in which said outer shape of said first and second cores is cylindrical with a same outer diametric dimension, each of said emergence-profiler healing and coping guides capable of being interchangeably fitted over each of said cores.

20. The set of dental components of claim 19 in which each of said cores has means on an outer surface for restraining said emergence-profiler healing and coping guides from rotating around a tubular axis of said cores.

21. The set of dental components of claim 16 in which said first core has a surface forming a section of said emergence profile in said aperture.

22. The set of dental components of claim 21 in which said second core has a surface for substantially fitting within said section of said emergence profile in said aperture formed by said surface of said first core.

23. The set of dental components of claim 16 in which said emergence-profiler coping guide is a transfer coping.

24. The set of dental components of claim 23 in which said means for fixing said second core on said root means includes a wide-headed impression-coping screw.

25. The set of dental components of claim 23 in which said first and second cores are substantially the same length.

26. The set of dental components of claim 16 in which said emergence-profiler coping guide is a pick-up coping.

27. The set of dental components of claim 26 in which said second core is longer than said first core.

28. The set of dental components of claim 27 in which said second core has means for retaining said second core in impression material, said retaining means including a groove.

29. A set of dental components for making a replacement tooth generally mimicking a contour and dimensions of an emergence profile of a natural tooth through gingiva overlying the root means, said gingiva having an aperture to said root means, said set comprising:

a first core for extending through said aperture in said gingiva, said first core for being attached to said root means;

an emergence-profiler healing guide having an exterior surface contoured and dimensioned for forming said emergence profile in said aperture, said exterior surface being made of a plastic material, said emergence-profiler healing guide surrounding and engaging said first core;

a second core for extending through said aperture in said gingiva, said second core for being attached to said root means; and an emergence-profiler coping guide having an exterior surface contoured and dimensioned for substantially fitting within said aperture, said exterior surface being made of a plastic material, said emergence-profiler coping guide surrounding and engaging said second core.

30. The set of dental components of claim 29 wherein said first and second cores have structures for retaining said emergence-profiler healing and coping guides against rotation.

31. A method of preparing an artificial tooth for placement in a site in a mouth having root means with an overlying gingiva layer and an opening in said overlying gingiva layer to said root means, said method comprising the steps of:

forming said opening to said root means with a healing component, said healing component including a first core and an emergence-profiler healing guide having a shape corresponding to a shape of a transmucosal portion of a natural tooth formerly at said site, said emergence-profiler healing guide having an exterior surface being made of a plastic material;

making a model of said site so as to substantially replicate said opening;

forming said artificial tooth on said model; and installing said artificial tooth to said root means.

32. The method of claim 31 wherein said step of making a model includes the steps of:

removing said healing component;

installing an impression component; and taking an impression over said impression component.

33. The method of claim 32 wherein said impression component includes a second core and an emergence-profiler coping guide, said emergence-profiler coping guide having substantially a same shape as said opening.

34. The method of claim 31 wherein said emergence-profiler healing guide is made entirely of a plastic material.

35. The method of claim 31 wherein said step of forming said opening includes the steps of installing said first core on said root means, and fitting said emergence-profiler healing guide over said first core.

36. The method of claim 31 wherein said emergence-profiler healing guide includes a shell and a filling material to be placed within said shell.

* * * * *